(12) United States Patent
Broersma

(10) Patent No.: US 6,957,447 B1
(45) Date of Patent: Oct. 25, 2005

(54) MONOLITHIC PAINTBALL MASK

(75) Inventor: Lester V. Broersma, San Diego, CA (US)

(73) Assignee: JT USA, LLC, Corona, CA (US)

( * ) Notice: Subject to any disclaimer, the term of this patent is extended or adjusted under 35 U.S.C. 154(b) by 0 days.

(21) Appl. No.: 10/971,946

(22) Filed: Oct. 22, 2004

(51) Int. Cl.$^7$ ............................. A42B 1/00; A61F 9/02
(52) U.S. Cl. ........................... 2/9; 2/423; 2/425; 2/427
(58) Field of Search .................. 2/9, 425, 423, 2/426, 427, 424, 428, 452, 454, 436, 206; 128/201.27, 201.15, 201.17, 201.23, 201.22, 128/863, 206.22, 206.21, 206.28; D24/110.2, D24/110.3

(56) References Cited

U.S. PATENT DOCUMENTS

| | | | |
|---|---|---|---|
| 2,680,882 A * | 6/1954 | Hirschmann et al. | 264/292 |
| 3,103,667 A * | 9/1963 | Rogowski | 2/9 |
| 3,152,588 A * | 10/1964 | Rogowski | 128/206.12 |
| 3,274,614 A * | 9/1966 | Boyer | 2/427 |
| 3,705,760 A * | 12/1972 | Langendorfer et al. | 351/44 |
| 3,845,768 A * | 11/1974 | Garrahan | 128/206.24 |
| D233,956 S * | 12/1974 | Stegmon | D24/110.2 |
| 4,610,036 A * | 9/1986 | LaPrairie | 2/12 |
| 4,837,862 A * | 6/1989 | Heil | 2/12 |
| 5,018,223 A | 5/1991 | Dawson et al. | |
| 5,088,114 A * | 2/1992 | Salce et al. | 2/9 |
| 6,381,749 B1 | 5/2002 | Cyr | |
| 2003/0221246 A1* | 12/2003 | Schary et al. | 2/453 |
| 2005/0066967 A1* | 3/2005 | Jacob | 128/201.27 |

FOREIGN PATENT DOCUMENTS

| | | | | |
|---|---|---|---|---|
| EP | 72229 A1 * | 2/1983 | | A62B 18/02 |
| FR | 2607916 A1 * | 6/1988 | | F41H 1/04 |

\* cited by examiner

Primary Examiner—Rodney M. Lindsey
(74) Attorney, Agent, or Firm—Charmasson, Buchaca & Leach, LLP

(57) ABSTRACT

A combination wrap-around mask and goggle is made from a single transparent and flexible plastic material monolithically formed in a single cavity mold. The structure is devoid of any cavities or protrusions that could interfere with the easy withdrawal of the device from the mold. Front to back oriented ribs, gussets and fins are used to impart rigidity to various areas of the structure.

10 Claims, 2 Drawing Sheets

MONOLITHIC PAINTBALL MASK

FIELD OF THE INVENTION

This invention relates to goggles and face masks used by motorcycle riders, skiers, paintball game participants, and other sport enthusiasts.

BACKGROUND OF THE INVENTION

Goggles and face masks used in connection with a variety of sporting activities, and particularly motocross races and paintball games have been traditionally made as separate components having mating interfaces as disclosed in U.S. Pat. No. 6,381,749 Cyr. The goggle itself is often made of a molded frame capturing a single lens as disclosed in U.S. Pat. No. 5,018,223 Dawson et al. The complex shapes of the various components requires that they be formed in separate molds, and incorporate interconnecting structures.

A softer and opaque elastomeric material is usually used in forming the goggle frame, while the lens is made from a transparent, stiffer and more brittle plastic. The multiplicity of components and their complex shapes can seriously affect the manufacturing costs.

When used as a protective head gear in the game of paintball, the mask and goggle are often splattered with paint. Cleaning often requires dismantling and subsequent reassembly.

The stiffness of the mask material does not conform intimately with the facial features of the wearers and can create uncomfortable pressure points. In some cases, the stiffness of the material may limit the movements of the head.

The instant invention results from an attempt to simplify the manufacture of face masks and goggle combinations without compromising its protective qualities.

SUMMARY OF THE INVENTION

The principal and secondary objects of this invention is to provide paintball game players, motocross racers, skiers and other sport enthusiasts with an inexpensive and comfortable face mask, goggle, and ear cover device that can be conveniently manufactured in a simple injection molding or vacuum-forming process, and is devoid of any interconnecting structures so that it may be quickly and thoroughly cleaned without any kind of disassembling.

These and other valuable objects are achieved by using a relatively soft and pliable material such as polyurethane throughout the construction of the combination device, and by forming fins, gussets, and ribs in areas that must be rigidified such as the one framing the goggle lens. The device is devoid of any protrusion or cavity that would require inner surface of the mold orthogonal to the direction in which the structure is withdrawn from any female mold portion.

DESCRIPTION OF THE PREFERRED EMBODIMENT OF THE INVENTION

Figure 1:
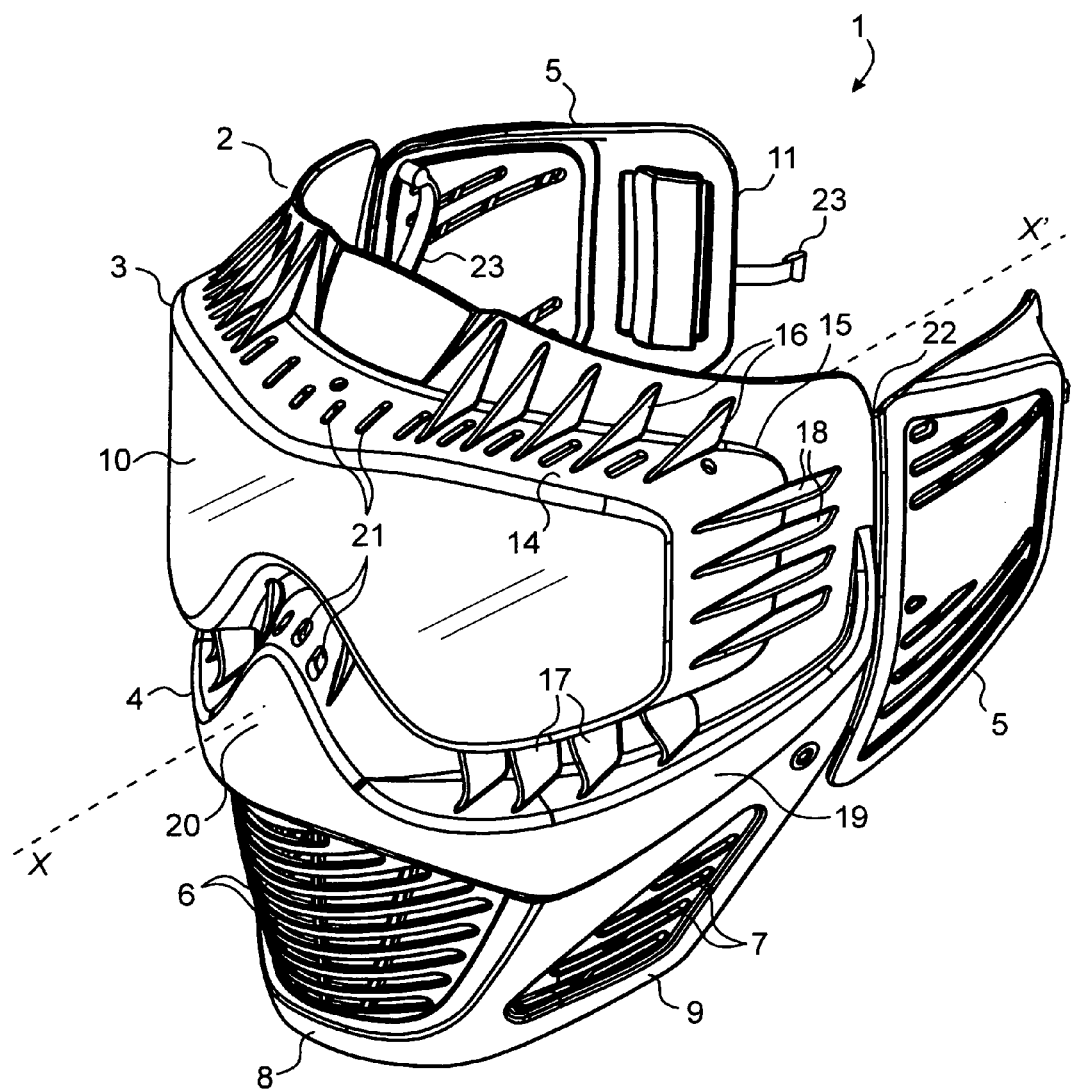
FIG. 1 is a perspective view of a mask and goggle combination according to the invention.
Figure 2:
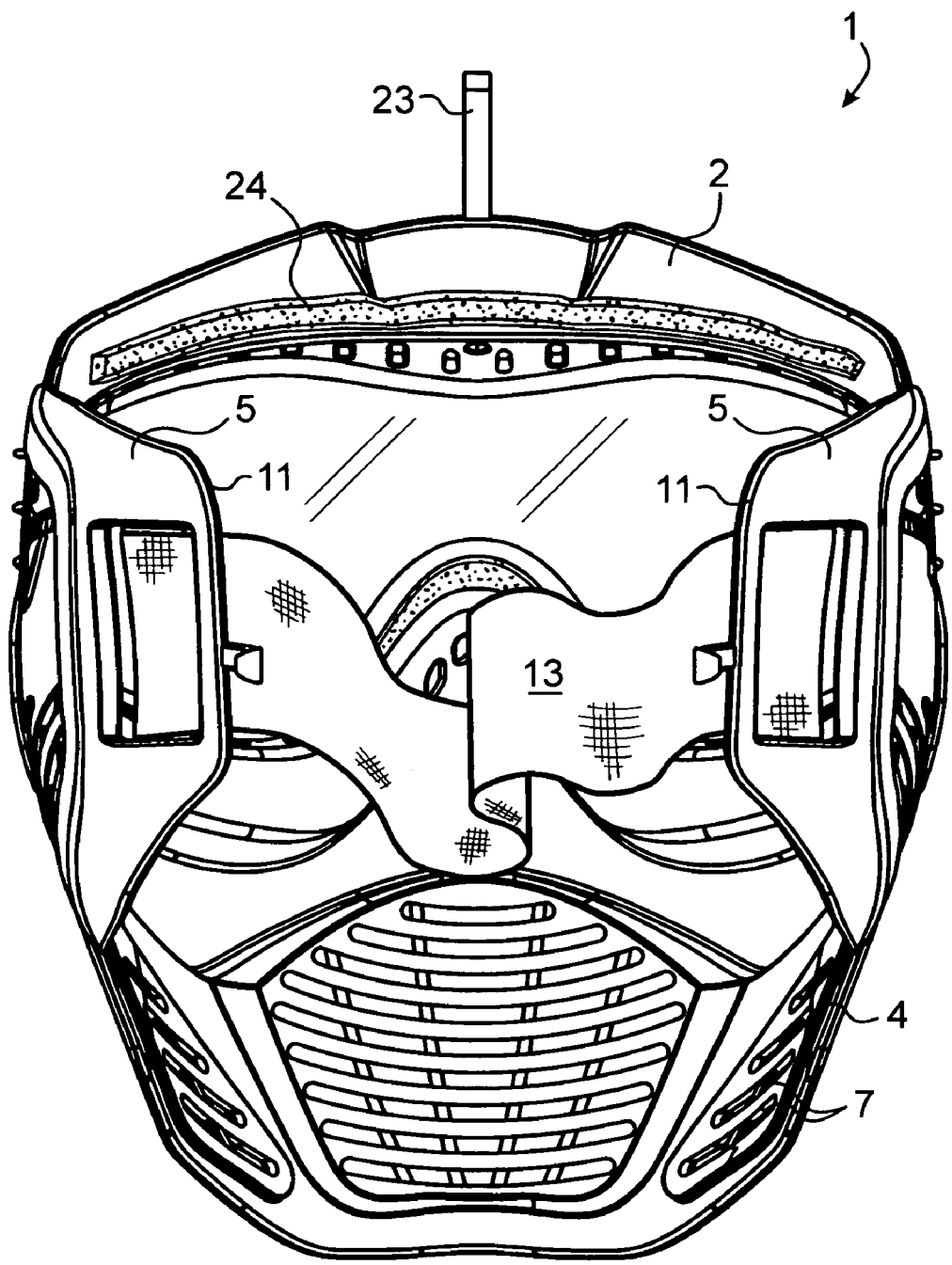
FIG. 2 is a rear view thereof.

Referring now to the drawing, there is shown a single piece face mask and goggle combination 1 according to the invention. The combination is molded from a relatively soft, pliable and transparent material such as polyurethane in a single cavity injection mold or vacuum form.

The mask portion comprises a frontal section 2 spanning the top of the goggle 3, a nose-and-mouth section 4, and a pair of ear covers 5 astride the goggle. Series of horizontal slots 6, 7 are provided for ventilation over the portion 8 covering the mouth and lateral portions 9 covering the cheeks for ventilation purpose. Each ear cover 5 terminates in a substantially vertical rear edge 11 along which is a cutout 12 engaged by a cinching elastic strap 13.

The goggle comprises a single arcuate lens 10 surrounded by a front-to-rear oriented flange 14 which meets along its peripheral rear edge 15, the frontal section 2, nose-and-mouth section 4, and ear covers 5.

A first series of triangular gussets 16 extending from the frontal section 2 to the upper part of the flange 14, and a second series of substantially trapezoidal gussets 17 extending from the lower portion of the flange to the nose-and-mouth portion 4 of the mask are used to stabilize and stiffen the flange and lens. A number of fins 18 extending along the lateral portion of the flange achieve the same functions as the gussets. The gussets 16, 17, the fins 18, and a stiffening rib 19 formed around the nose-and-mouth portion have a front-to-rear orientation which facilitates the withdrawal of the molding structure from its molding cavity. More specifically, the entire structure is devoid of any protrusion or cavity having rear-facing areas on the outer surface of the device. Indeed, any transversally oriented protrusion or cavity in relation to a front-to-rear axis X-X' passing through a nose tip 20 would not allow pulling the molded structure in a rearwardly direction out of a mold or form. In general, all outer surfaces of the mask and goggle combination are substantially tapering down from the rear toward the nose covering tip 20. The absence of any transversally oriented area on the outer surface of the mask that could interfere with the molding process constitutes an important feature of the mask and goggle combination.

Ventilation holes and slots 21 are also provided in the flange 14 and the nose tip area 20.

A vertical crease line is provided near the forward edge of each ear cover 5 to allow easy folding of the ear cover inwardly during shipping or storage of the device.

Pull tabs 23 are attached to the center of the frontal section 2 and the rear edges 11 of the ear covers, and are used to pull the molded structure out of the mold cavity. The pull tabs can be cut off after fabrication.

While the inner and outer surface of the lens 10 are kept very smooth to insure the transparency, all other outer surface can be conveniently pitted or textured to provide some opacity or for esthetic purpose.

Strips of padding foams 24 are glued along the upper and lower internal edges of the goggle for a more comfortable fit and to prevent blurring of the lense by perspiration and exhaling vapors.

While the preferred embodiment of the invention has been described, modifications can be made and other embodiments may be devised without departing from the spirit of the invention and the scope of the appended claims.

What is claimed is:

1. A mask and goggle device which comprises:
    a single lens goggle made of transparent pliable material;
    a mask including a frontal section above said goggle, a nose-and-mouth section below said goggle, and a pair of ear covers astride said goggles, each of said covers having a substantially vertical rear edge; and
    said mask being of the same material as said goggle, and being integrally formed with said goggle.

2. The device of claim 1, having outer surfaces substantially tapering down from rear-to-front about a central horizontal axis toward a nose covering tip, and being devoid of projections and cavities having rear-facing areas;
   whereby said device can be monolithically molded in a single cavity mold.

3. The device of claim 2, wherein said surfaces include reinforcing ribs, fins and gussets having a front-to-rear orientation.

4. The device of claim 1, wherein said goggle comprises a peripheral flange projecting rearwardly from said lens toward said frontal and nose-and-mouth sections; and
   a plurality of triangular gussets between said flange and said sections.

5. The device of claim 4, having vertical crease lines between said goggle and said covers;
   wherein said covers can be folded inwardly about said crease lines.

6. The device of claim 4, wherein said flange and sections have ventilation apertures.

7. The device of claim 1 which further comprises a cinching strap joined at opposite ends to said rear edges.

8. The device of claim 1 substantially devoid of any transversally oriented protrusion or cavity in relation to a front-to-rear axis.

9. The device of claim 1, wherein said material comprises polyurethane.

10. The device of claim 4, wherein said gussets have a front-to-rear orientation.

* * * * *